United States Patent
Sue et al.

(10) Patent No.: US 6,419,956 B1
(45) Date of Patent: Jul. 16, 2002

(54) ODOR-MASKING COATING FOR A PHARMACEUTICAL PREPARATION

(75) Inventors: I-Lan T. Sue, San Jose; Pou-Hsiung Wang, Pasadena, both of CA (US)

(73) Assignee: Ancile Pharmaceuticals, San Diego, CA (US)

( * ) Notice: Subject to any disclaimer, the term of this patent is extended or adjusted under 35 U.S.C. 154(b) by 0 days.

(21) Appl. No.: 09/475,750

(22) Filed: Dec. 30, 1999

(51) Int. Cl.[7] .............. A61K 9/32; A61K 9/34; A61K 9/36; A61K 9/38; A61K 9/40
(52) U.S. Cl. .......... 424/480; 424/479; 424/482; 514/770; 514/772.3; 514/773; 514/781; 514/777; 514/782; 514/778; 514/779; 514/774; 514/786
(58) Field of Search .............. 424/474, 475, 424/479, 480, 482, 493, 494, 497

(56) References Cited

U.S. PATENT DOCUMENTS

| | | | |
|---|---|---|---|
| 3,989,823 A | * 11/1976 | Di Costanzo | 424/195 |
| 4,828,845 A | * 5/1989 | Zamudio-Tena et al. | 426/5 |
| 5,211,948 A | * 5/1993 | Cerise et al. | 424/195.1 |
| 5,626,875 A | * 5/1997 | Ballester Rodes et al. | 424/464 |
| 5,707,630 A | * 1/1998 | Morrow | 424/195.1 |
| 5,916,595 A | 6/1999 | Chen et al. | 424/480 |
| 5,976,586 A | * 11/1999 | Feller | 426/89 |

FOREIGN PATENT DOCUMENTS

| | | | |
|---|---|---|---|
| FR | 2699075 | 6/1994 | |
| FR | 2738833 | 3/1997 | |
| JP | 4-173741 | * 6/1992 | ......... A61K/35/78 |
| WO | WO97/47311 | 12/1987 | |

OTHER PUBLICATIONS

Aqueous Extract of Valerian Root, Leathwood, et al, pp. 65–71, Ankho, Dec. 1981.*
Aqueous Polymeric Coatings, Drugs & RX Sciences, McGinity, vol. 79, Jan. 1997.*

* cited by examiner

*Primary Examiner*—James M. Spear
(74) *Attorney, Agent, or Firm*—Knobbe Martens Olson & Bear LLP

(57) ABSTRACT

A coating for masking or reducing the detectable presence of certain characteristic odor or odors, taste or tastes of pharmaceutical preparations, particularly Valerian extracts, is described. The coating comprises from one to three coating compartments, in any combination or as a single-layer amalgam. The first coating compartment comprises a hydroxyalkyl cellulose and an anti-tackiness agent The second coating compartment may comprise a sugar and at least one anti-tackiness agent. The third coating compartment may comprise a methacrylate copolymer, a hydroxyalkyl cellulose and an anti-tackiness agent.

28 Claims, 1 Drawing Sheet

ODOR-MASKING COATING FOR A PHARMACEUTICAL PREPARATION

BACKGROUND OF THE INVENTION

1. Field of the Invention

The present invention generally relates to tablet coatings. More particularly, the invention relates to a coating useful in masking the odor of pharmaceutical preparations, particularly extracts from the plant Valerian.

2. Description of the Related Art

Pharmaceutical preparations are sometimes associated with unpleasant odors. For example, the strong, unique, unpleasant, and characteristic odor of extracts of the root of the plant *Valeriana officinalis* L. are well known.

Methods are known for masking such odors. For example, and most typically, flavoring agents may be added to a medicaments (e.g., a pharmaceutical or other formulation) to change the taste of oral medications. Alternative methods to change the smell or taste of medicaments are available, such as smell masking or taste masking. One of the common goals of these various methods of taste and smell masking is to make the medication more appealing to consumers. This goal may lead to an increase in consumer compliance with prescribed and/or recommended dosing regimens.

Extracts of the root of the plant *Valeriana officinalis* L. (*V. officinalis* L.) have been used for medicinal purposes for over a century. Certain valerian extracts, including aqueous extracts, are known to have sedative and anxiolytic effects, but the active components have not been clearly and positively identified. See Leathwood P. D., and Behavior, 17:65–71 (1982); Leathwood P. D. and Chauffard F., "Aqueous extract of valerian reduces latency to fall asleep in man," Planta Medica, 2:144–148 (1985). Such effects are described by Balandrin et al. in U.S. Pat. No. 5,506,268, which is incorporated by reference herein in its entirety. Presently, valerian is available as dietary supplements; these dietary supplements primarily comprise dried root or extracts from the root, formulated into tablets or gelatin capsules. Each dose contains between approximately 50 mg and approximately 1 gram of dried root or extract.

It is not known in the art which constituents of *Valeriana officinalis* L., and/or of the other heretofore unidentified members of the Valerianaceae family, are responsible for the sedative and/or anxiolytic action of valerian extracts. Nonetheless, the valepotriates (iridoids) as well as valerenic acid, a sesquiterpenoid compound, and the derivatives of valerenic acid (for example, acetoxyvalerenic acid and hydroxyvalerenic acid) along with the kessane derivatives, valeranone, valerenal, and certain amino acids are present in valerian extracts. Of these components, the valepotriates and valerenic acids are generally considered to contribute to the sedative action of valerian extracts, but have not been clearly and positively identified as such. See Hendriks H. et al., "Pharmacological Screening of valerenal and some other components of essential oil of *Valeriana officinalis*," Planta Medica, 42, 62–68 (1981); Bos R. et al., "Analytical aspects of phytotherapeutic valerian" (1996); Houghton P. J., Valerian. The Genus Valeriana. Harwood Academic Publishers, London. (1997).

The therapeutic benefits of extracts of the root of the plant *Valeriana officinalis* L. are well-known, and are described in the literature. Such extracts do have a strong, identifying, characteristic and unpleasant smell or odor and an associated disagreeable taste. This characteristic odor and/or this characteristic taste make consuming sufficient therapeutic quantities of the extracts of the root of the plant *Valeriana officinalis* L. difficult for a substantial percentage of the population. In one reported effort to mask the smell of an extract of the root of a plant of the genus Valeriana, see U.S. Pat. No. 5,211,948 to Cerise et al., the degradation products of valepotriates are identified as the odor causing agents in the aqueous extraction of Valerian root. This reference describes that the odors may be eliminated by, for example, the steps of concentrating the aqueous extract and precipitating the resultant extract with acetone. The precipitated components may then be removed from the rest of the extract via centrifugation. The reference describes that the valerenic acids found in the roots remain present in the resulting extract, and that the resulting extract has a neutral taste and smell. However, as also described in U.S. patent application Ser. No. 60/173,983, entitled "Process For Reducing The Odor Of Valeriana," and filed on this date and herewith, the disclosure of which is hereby incorporated by reference herein, (1) when an aqueous extract of Valerian root was produced according to a method of the '948 patent, it was observed that the extract still contained the significant, distinctive, characteristic and pungent smell and associated taste of Valeriana, (2) inconsistent with the teachings of U.S. Pat. No. 5,211,948 to Cerise et al., the characteristic odor of *V. officinalis* extract may be significantly reduced via the addition of a sufficient amount of a chemical base to the extract formulation, and (3) the addition of base reduces the pungent smell by lowering the vapor pressure of isovaleric acids, and other like acidic components of a *V. officinalis* extract, which are therefore the source of the characteristic odor and taste.

Certain conventional approaches for masking odors of medicinal preparations, especially tablets, also utilize sugar-coating technology. Such conventional technology typically requires the use of a non-perforated coating pan and generally requires extensive materials, long processing times, multiple stages/layers, and experienced scientists to obtain products with acceptable quality, i.e. odor masking and smooth appearance. Sugar-coating technology has been applied to the commercially available valerian tablet product, Sedonium®, manufactured by Lichtwer Pharma AG, Berlin, Germany. In this product, the weight of the sugar coat applied to each tablet is nearly a half of the core tablet weight.

In the pharmaceutical industry, an alternative coating technique, applicable to tablets, film coating, is generally performed in a perforated coating pan or fluid-bed particle coater. The benefits of film coating, with respect to sugar coating, include: (1) shortened processing time; (2) substantially reduced coating material quantity; (3) easily controlled processing conditions; (4) improved reproducibility from small scale to large scale; and (5) increased selection options for coating materials or polymers.

There is a need in the art for an alternative coating capable of masking odors of various pharmaceutical preparations. The present invention addresses this need, among others.

SUMMARY OF THE INVENTION

A pharmaceutically-inert coating is described that is effective in masking the characteristic, unpleasant odor (and/or taste) of a plant or plant extract, and particularly of the root or an extract of the root of the plant Valerian. The coating comprises one or more of the following coating compartments: a first coating compartment comprising a hydroxyalkyl cellulose and an anti-tackiness agent and, optionally, a plasticizer; a second coating compartment comprising a sugar and at least one anti-tackiness agent; and a third coating compartment comprising a methacrylate copolymer, a hydroxyalkyl cellulose and an anti-tackiness agent. The hydroxyalkyl cellulose of the first coating compartment is preferably selected from the group consisting of hydroxyethyl cellulose and hydroxypropyl cellulose. The anti-tackiness agent of the first coating being preferably selected from the group consisting of talc, silicon dioxide, silica hydrogel, microcrystalline cellulose, alkali stearates, and starch. The second coating compartment preferably also comprises a plasticizer; the plasticizer being preferably selected from the group consisting of propylene glycol, glycerin, trimethylolpropane, polyethylene glycols, dibutyl sebacate, acetylated monoglycerides, diethylphthalate, triacetin, glyceryl triacetate, acetyltriethyl citrate and triethyl citrate. The third coating compartment may also comprise a plasticizer; the plasticizer being preferably selected from the group consisting of propylene glycol, glycerin, trimethylolpropane, polyethylene glycols, dibutyl sebacate, acetylated monoglycerides, diethylphthalate, triacetin, glyceryl triacetate, acetyltriethyl citrate and triethyl citrate; and the third compartment may also comprise a water soluble polymer, preferably being selected from the group consisting of hydroxypropyl cellulose, hydroxypropyl methylcellulose, acacia, sodium carboxymethylcellulose, dextrin, alginic acid, ethylcellulose resin, gelatin, guar gum, liquid glucose, methylcellulose, pregelatinized starch, sodium alginate, starch, zein, polyvinylpyrrolindone, vinylpyrrolidone-vinyl acetate copolymer, vinyl acetate-crotonic acid copolymer and ethyl acrylate-methacrylic acid copolymer.

BRIEF DESCRIPTION OF THE DRAWINGS

The accompanying drawings, which are incorporated in and form part of the specification, merely illustrate embodiments of the present invention. Together with the remainder of the specification, they are meant to serve to explain the principles of the invention to those of skill in the art. In the drawings.

DETAILED DESCRIPTION OF THE PREFERRED EMBODIMENTS

Figure 1:
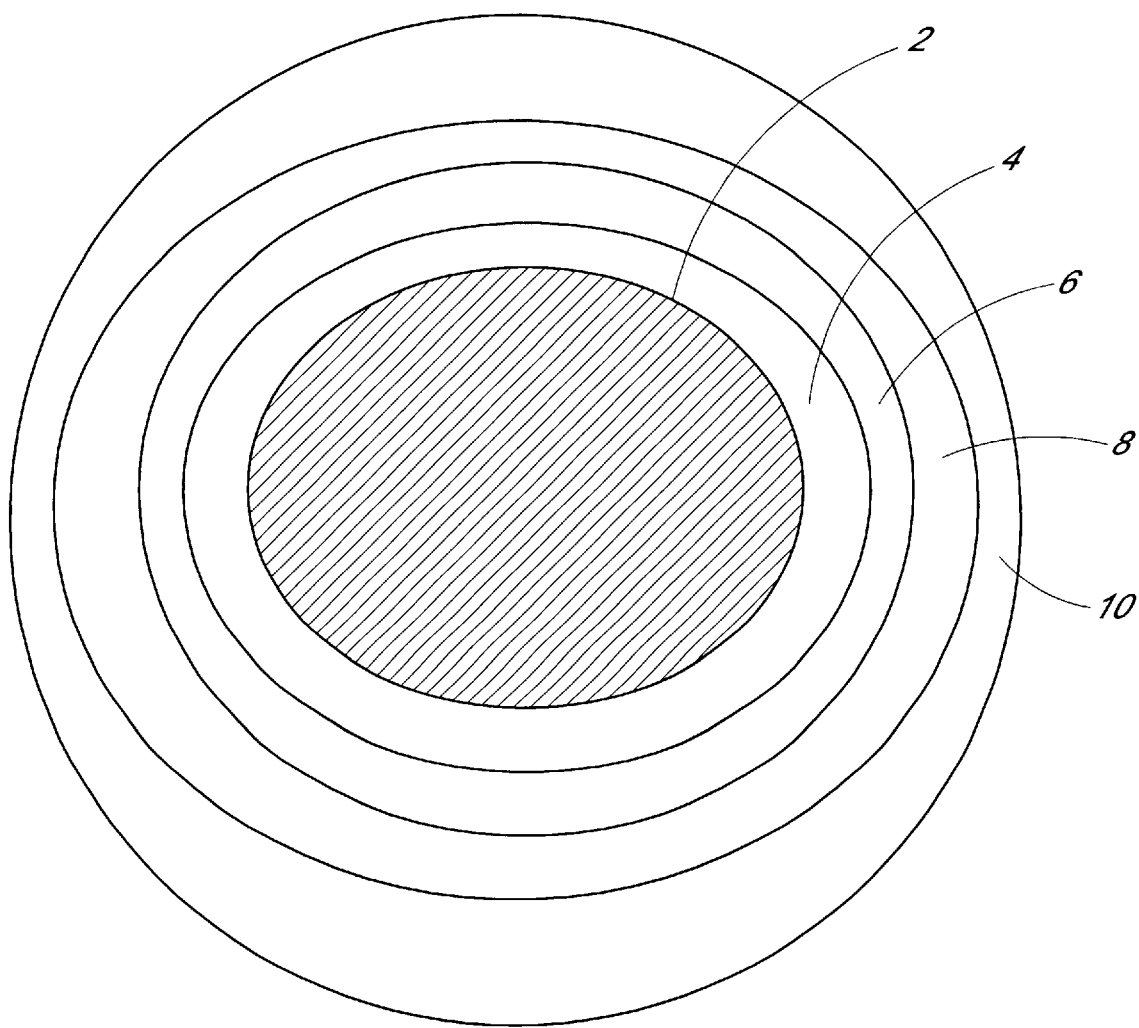
FIG. 1 depicts a cross-sectional view of a preferred embodiment of the multilayer odor-masking coating of the present invention. A tablet dosage form is shown as an example, and the pharmaceutically active tablet core, 2, is cross-hatched.

The present invention provides a coating for masking the odor of pharmaceutical preparations. Although the masking of odor from valerian extracts is described herein, the coating and coating methods of the present invention may be applied to any pharmaceutical formulation in tablet or capsule form which has a strong or unpleasant odor.

The method described in the present application uses film coating technology. This method provides an advantage of allowing for the use of a reduced amount of coating materials and the advantage of improved odor-masking efficiency when compared to commercially available Valerian tablets. According to the present invention, odor reduction may be achieved with a coating material amount of about, for example, 25% or less of the core tablet weight, compared to the about 50% for commercially available products.

As used herein, the terms "Valeriana" and "Valerian" refer to any plant of the Valerianaceae, and therefore refers, at least to, the plant designated *Valeriana officinalis* L. This species includes all recognized subspecies of *Valeriana officinalis* L. Some of these subspecies are also commonly referred to, in alternative taxonomic systems, as: *Valeriana exaltata* J. C. Mikan, *Valeriana nitida* Kreyer, *Valeriana palustris* Wibel, *Valeriana wolgenis* Kazak, *Valeriana grossheimii* Vorosch, *Valeriana collina* Wallr, *Valeriana Rossica* P. A. Smirn, *Valeriana spryngini* P. S. Smirn, *Valeriana angustifolia* Tausch, *Valeriana tenuifolia* Vahl, *Valeriana wallrothii* Kreyer, *Valeriana ucrainica* Demjan, *Valeriana sambucifolia* J. C. Mikan, *Valeriana excelsa* Poir, and *Valeriana officinalis* L.subsp. excelsa (Poir.) Rouy. Plants of the species *Valeriana officinalis* L. may be characterized as follows: These plants grow from a short rhizome to 2 m high, flowers, and then die back again in the winter. These plants have pinnately-divided leaves with six to ten pairs of lance-shaped leaflets, and bear many small white or pink flowers in a dense head of several stalked clusters. The heads bare small (5 mm) tapered seeds.

As used herein, the terms "reduces," "reduced," or "reducing," when used to refer to a particular odor or taste characteristic, refers to any observable lessening of that characteristic when the method or composition of the present invention is compared to prior art methods or compositions.

As used herein, the term "roof" or "roots" refers to all of subterranean portion of a specifically or generically identified plant, including, but not limited to, the roots, the rhizomes, and the stolons of the specifically or generically identified plant. Where the term "roots" is not modified by a specifically or generically identified plant, it will be understood that the term refers to the roots of the species, and to sub-species of, *Valeriana officinalis* L.

As used herein, the terms "odor," "smell," and "scent" refer to olfactory recognition of any particular or group of particular gases. Preferably, the olfactory recognition refers to mammalian, and most preferably human, olfactory recognition. Such recognition was determined by observation by the inventors, and may alternatively be determined by a cross-section of the population or by quantitative or qualitative recognition devices known to those of skill in the art.

With reference to a preferred embodiment, as depicted in FIG. 1, each of the three inner coating compartments can be applied alone or in combination with other layers to mask the odor of the core tablet. In other words, the coating of the invention may comprise one, two or all three of the three inner layers, in any combination or in any order or arrangement. The sequence of coating layer application can be altered to accommodate product or manufacturing needs. An optional cosmetic color coat, which need not have an odor-masking effect, may be applied as a separate layer or combined in one or more of the polymer layer or layers. Pharmaceutical coatings are described in detail by Bauer et al. in *Coated Pharmaceutical Dosage Forms: Fundamentals, Manufacturing Techniques, Biopharmaceutical Aspects, Test Methods and Raw Materials*, CRC Press, Boca Raton, Fla., 1998.

BRIEF DESCRIPTION OF THE DRAWING

The coating compartments of a preferred embodiment of the present invention are shown schematically in FIG. 1. Tablet core 2, and cross hatched, with reference to FIG. 1, is coated with first coating compartment 4 which preferably comprises a hydroxyalkyl cellulose in which the alkyl group has between one and ten carbon atoms, and an anti-tackiness agent. The hydroxyalkyl cellulose functions as one or more of the following: film former, coating agent, suspending agent, tablet excipient, demulcent and viscosity-enhancing agent. These hydroxyalkyl celluloses include, but are not limited to, hydroxypropyl cellulose, hydroxymethyl cellulose and hydroxyethyl cellulose. Hydroxypropyl cellulose is a non-ionic, water-soluble polymer and is used in films and coatings due to its excellent film flexibility, toughness, and barrier to oil and fat. Hydroxyethyl cellulose is a non-ionic, water-soluble polymer, which has been used to form matrix tablets to obtain desired modified release properties. Either or both of these polymers may be incorporated into the first coating compartment. Hydroxypropyl cellulose includes, but is not limited to, various grades of Klucel® (Hercules, Aqualon Division). Hydroxyethyl cellulose includes, but is not limited to, various grades of Natrosol® (Hercules, Aqualon Division). In a preferred embodiment, the amount of hydroxyalkyl cellulose in the first coating compartment is between about 10–70% w/w.

Anti-tackiness agents reduce the tackiness (stickiness) of the pharmaceutical preparations. These agents include, but are not limited to, talc, silicon dioxide, silica hydrogel, microcrystalline cellulose, alkali stearates, and starch. In a preferred embodiment, the amount of anti-tackiness agent in the first coating compartment is between about 20%–60% w/w.

Optionally, a compound which facilitates the coating process is added. Many such compounds are known in the art and include ethylcellulose, methylcellulose and carboxymethyl ethylcellulose. A preferred additive is hydroxypropyl methylcellulose. Types of hydroxymethyl cellulose include, but are not limited to, various grades of Methocel® (e.g., Methocel A, E, F, and K; Dow Chemical, Midland, Mich.), Pharmacoat® (e.g., Pharmacoat 606, 603, 615, and 904) (Shin-Etsu Chemical Co., Ltd., Japan/Dynamix Cosmo Private Ltd., Singapore), and Metolose SM (Shin-Etsu Chemical Co., Ltd., Japan/Dynamix Cosmo Private Ltd., Singapore). In a preferred embodiment, the coating process-facilitating compound is added in an amount of up to 20% w/w.

Optionally, a plasticizer may be incorporated into the first coating compartment Plasticizers are compounds which impart flexibility, workability or stretchability to the coating. Plasticizers include, but are not limited to, propylene glycol, glycerin, trimethylolpropane, polyethylene glycols, dibutyl sebacate, acetylated monoglycerides, diethyl phthalate, triacetin, glyceryl triacetate, acetyltriethyl citrate, and triethyl citrate. In a preferred embodiment, the plasticizer is added in an amount of up to 20% w/w.

The second coating compartment 6 comprises a sugar and one or more anti-tackiness agents Sugars increase the palatability of the preparation. Suitable sugars for incorporation into the second coating compartment 6 include, but are not limited to, sucrose, dextrose, dextrin, maltose, glucose, fructose, mannose, sorbitol, lactose, mannitol, xylose and the like. The amount of sugar incorporated into the second coating compartment is generally about 20–80% w/w. The amount of anti-tackiness agent incorporated into the second coating compartment is generally about 5–50%. In a preferred embodiment, two anti-tackiness agents are used, one of which is either talc or silicon dioxide. Preferably silicon dioxide is one of anti-tackiness agents in a sugar system such as that of the preferred embodiment of the second coating compartment described herein.

Optionally, one of the following additives may be incorporated into the second coating compartment to facilitate the coating process: polyvinyl pyrrolidone, vinylpyrrolidone acetate copolymer, vinyl acetate-crotonic acid copolymer, ethyl acrylate-methacrylic acid copolymer, hydroxypropyl cellulose, gelatin, acacia, or other cellulose derivatives. These additives are generally added in an amount of about 0–30% w/w. Optionally, a plasticizer may be incorporated into the second coating compartment. The amount of plasticizer is typically about 0–20% w/w.

The third coating compartment 8 comprises a polymethacrylate, a hydroxyalkyl cellulose in which the alkyl group has between one and ten carbon atoms, and an anti-tackiness agent. Polymethacrylates include, but are not limited to, methacrylic acid/methyl methacrylate copolymers, methacrylic acid/ethylacrylate copolymers aminoalkylmethacrylate copolymers, and ammoniomethacrylate copolymers. In general, the amount of methacrylate copolymer incorporated into the third coating compartment is between about 1–30% w/w and the amount of hydroxyalkyl cellulose is between about 5 and 70% w/w.

Methacrylate copolymers are water-insoluble, and will hydrate and swell in the presence of water. Eudragit NE30D (Rohm) is one example of this series of polymers and is an aqueous dispersion of a neutral copolymer containing ethyl acrylate and methyl methacrylate. This series of polymers is widely used in functional coatings to achieve delayed or controlled release of a pharmaceutical agent. In some cases, these types of polymers are used in matrix tablets due to their modified drug release properties. These polymers can be used alone or in combination with one or more other members of the series.

Optionally, a compound which facilitates the coating process is added. A preferred additive is hydroxypropyl methylcellulose. A plasticizer may also be added. The preferred amount of each of these compounds to be incorporated into the third coating compartment is between about 0–20% w/w.

In another preferred embodiment, water-soluble, non-Eudragit type polymers or compounds are combined with Eudragit type (methacrylic) polymers to achieve odor masking without prolonged drug release. Such water-soluble polymers or compounds include, but are not limited to, hydroxypropyl cellulose, hydroxypropyl methylcellulose, acacia, sodium carboxymethylcellulose, dextrin, alginic acid, ethylcellulose resin, gelatin, guar gum, liquid glucose, methylcellulose, pregelatinized starch, sodium alginate, starch, zein, polyvinylpyrrolindone, vinylpyrrolidonevinyl acetate copolymer, vinyl acetate-crotonic acid copolymer, and ethyl acrylate-methacrylic acid copolymer. The percentage of selected chemicals in the film may vary widely depending on the nature of selected material. Plasticizer may be included if necessary to improve the flexibility and appearance of the film.

Optionally, a fourth coating compartment 10 may be applied as a cosmetic color coat which need not function as an odor-masking coat. Optionally, the color coat may be combined with one of the other three coating compartments. In one embodiment, the color coat is Opadry II (32K 11498), Green (®, Colorcon inc.). Alternative components for the color coat, and the selection of same, are within the skill of those in the art.

Other ingredients such as lubricants, color pigments, surfactants, glidants, etc. may be included in one or more of the coating compartments to assist coating operation and/or improve film quality. The selection of such alternative ingredients is within the skill of those in the art. Lubricants may include, but not limited to, calcium stearate, hydrogenated vegetable oils, magnesium stearate, mineral oil, polyethylene glycols, stearic acid, sodium benzoate, sodium lauryl sulfate, leucine, and sodium stearyl fumarate. The percentage of total solids in a preferred selected solvent or solvent mixture may be in the range of about 5% to 50% w/w, and preferably about 8–12% w/w.

All of the coating layers described herein can be applied using conventional film coating technology well known in the pharmaceutical industr. See, for example, *Remington's Pharmaceutical Sciences* (A. R. Gennaro edit. 1985), Mack Publishing Co, Easton, Pa. For example, film coating may be performed in a perforated coating pan or fluid-bed particle coater. Each coating layer may be applied to either tablet or multiparticular medicinal preparations. Depending on the nature of the selected coating materials, the following solvents, whether used alone or in combination, may be used to prepare coating solution or suspension: water, ethanol, methanol, acetone, isopropyl alcohol, acetic acid, glycerin, and methylene chloride, etc. Examples of coating materials contemplated for use in the present invention is presented in the examples.

As described above, the conventional sugar-coating process typically involves the use of a traditional non-perforated coating pan. With the presence of proper additives such as auxiliary film formers, anti-tackiness agents, and/or water insoluble fillers as described in the present invention, acceptable sugar film can be achieved using a perforated coating pan or fluid-bed particle coater.

Either a perforated coating pan or a fluid-bed particle coater may be employed to apply coating materials, as described above, to medicinal preparations containing extracts from the plant Valerian. A preferred process for the extraction of Valerian root is described in copending U.S. patent application Ser. No. 09/358,375, filed Jul. 21, 1999, and entitled "Process for the Extraction of Valerian Root" the entire contents of which are incorporated herein by reference. These extracts comprise essential oils, valerenic acids, kessane derivatives, valeranone, valerenal, fatty acids, carbohydrates and certain amino acids, and may, depending on the extraction condictions, include valepotriates (iridoids).

The valerian root extraction process for the preparation of the pharmaceutically active tablet core 2 component of tablets of the present invention, may involve heating a mixture of the roots and an alcoholic extraction solvent for an extended period of time to obtain valerenic acid and valerenic acid derivatives in the extract, and to significantly reduce the amount of valepotriates in the extract. This extraction process, as described in co-pending U.S. patent application Ser. No. 09/358,375, which is hereby incorporated by reference, when compared to currently available processes, significantly reduces the amount of valepotriates in the valerian extract, while maximizing the amount of valerenic acid and of valerenic acid derivatives.

The process of preparing a formulation of the present invention therefore may include an extraction process. The complete process for preparing such a formulation is described to place the extraction process in the context of the preparation of the pharmaceutically active formulation and the coating and coating methods of the present invention. The following five steps comprise the process for preparing such a formulation: Pre-Extraction Processing of the Root, Extraction, Drying and Milling of the Drug Substance, and Formulation of a Tablet or Capsule. Additional or alternative steps, as well as the use of different pharmaceutical formulations, may be added without departing from this process.

Pre-Extract Processing of the Root. The roots may be prepared for extraction by grinding, chipping, or pulverizing to a powder in a hammermill, or a like instrument, as will be appreciated by those of skill in the art. After such pre-extraction processing, preferably at least 70%, 75%, or 80%, and most preferably 85% or 90% of the mass of the roots pass through a Tyler 20-mesh screen. Also preferably, the raw or processed roots are stored in a durable non-reactive, preferably plastic, and more preferably polyethylene, container or containers. These containers may be doubly-lined with bags of like material and closed or closeable with a lid composed of like material.

Extraction. The valerian root, whether, as preferred, processed as described above or in an unprocessed state, may be added to an extraction solvent. Most preferably, the root is added in a ratio of approximately one kilogram to approximately five liters of extraction solution. The extraction solvent preferably is an alcoholic extraction solution, comprising between approximately 30% to approximately 100% (volume/volume; v/v) alcohol and between approximately 70% (volume/volume; v/v) to 0% (v/v) water. Preferably, the alcoholic extraction solvent comprises approximately 50% to approximately 100% (v/v), approximately 55% to approximately 95% (v/v), approximately 65% to approximately 85% (v/v), and approximately 65% to approximately 75% (v/v) alcohol. Specifically, the alcoholic extraction solvent may comprise approximately 50% (v/v), approximately 60% (v/v), approximately 70% (v/v), approximately 80% (v/v), approximately 90% (v/v) alcohol and approximately 100% alcohol. The alcohol used in the alcoholic extraction solvent is fully miscible in water, and is preferably denatured ethanol (95% ethanol+5% methanol), but may be any $C_1$–$C_6$ alcohol, including but not limited to methanol, ethanol, n-butanol, isobutanol, n-propyl alcohol, and isopropyl alcohol.

The mixture of root and alcoholic extraction solvent may be stirred by any mechanical device conventionally known for such purpose, including but not limited to an overhead stirrer, a magnetic stirrer assembly, and/or a built-in stirrer, and may be suitable for or adapted to the particular extraction vessel employed. The mixture may be heated to between approximately 65° C. and 85° C., and more preferably between approximately 70° C. and 80° C., or alternatively, the temperature of reflux. Specifically, the mixture may be heated to 50°, 55°, 60°, 65°, 70°, 75°, 77°, or 80° or reflux. Various conventional methods may be used to heat the mixture, including but not limited to heating mantels or other resistive heating coils.

Preferably, the mixture is heated to any of the above-described temperature for at least one, one and one-half, two, two and one-half, three, three and one-half hours, four, or up to five hours. These durations, most preferably the latter three durations, are selected to significantly reduce the level of valepotriates relative to the initial value, preferably at least a 50% reduction. (Final Value/Initial Value=Percent Reduction). More preferably the reduction is by 60%, 70%, 75%, 80%, 90%, 95%, and most preferably 100% of the detectable level of valepotriates. In the latter case, the valepotriate level is not detectable by conventional techniques. The final valepotriate level may be obtained and may also be compared to that found in commercial valerian extracts.

Optionally, the mixture may then be cooled, preferably to room temperature or alternatively to a temperature above room temperature, including 30° C., 35° C., 40° C., 45° C., and 50° C. The solids may then be separated from the liquid (by filtration or centrifugation or any other conventional method for separation). The extraction vessel and the separated solids may be rinsed with the extraction solvent, described above. For such a rinse, from approximately four liters, three liters, two liters, or preferably one liter of extraction solvent may be used for each kilogram of root initially extracted.

Also optionally, the filtrate containing the extracted material may be concentrated to an oily consistency under reduced pressure, including approximately 0.9, 0.8, 0.7, 0.6, and 0.5 atms, at a temperature above room temperature, including 30° C., 35° C., 40° C., 45° C., and 50° C. Optimally, a final volume of approximately 0.15 liters for each kilogram of root extracted is obtained.

Addition of Excipient to facilitate drying. The concentrate may be mixed with an excipient to facilitate drying. The excipient may be chosen from any commercially-available excipient or mixtures thereof, but is preferably selected from the following: Maltodextrin, NF, Tricalcium Phosphate, and Silicon Dioxide or other conventional excipient and any combination or mixture thereof as will be recognized by those of skill in the art. After addition of the excipient, the excipient will preferably comprise between approximately 10% and 40%, and more preferably between 20% and 25%, of the drug substance.

Drying and Milling of the Drug Substance. The concentrated valerian extract and excipient, if added, is dried under reduced pressure, including approximately 0.9, 0.8, 0.7, 0.6, and 0.5 atms, at a temperature slightly above room temperature, including 30° C., 35° C., 40° C., 45° C., and 50° C. Optimally, the drying is continuous until water content is equal to or less than 15%, 10%, or 5%, as measured by Karl Fischer analysis. The dried mixture may then be milled to a target of 80%, 85%, 90%, or 95% by weight passing through a size-exclusion screen of 60-mesh, 70-mesh, 80-mesh, 90-mesh, or 100-mesh.

Optionally drying of the extract may be accomplished by spray drying or any other conventional drying method as will be understood by one of ordinary skill in the art.

In a preferred embodiment, the dried extract is then formulated into a core for use as a tablet core having a pharmaceutical dosage form such as crystals, granules, pellets, tablets, and hard and soft gelatin capsules using convention methodology well known in the pharmaceutical arts. See, for example, *Remington's Pharmaceutical Sciences* (A. R. Gennaro edit. 1985), Mack Publishing Co, Easton, Pa., or latest edition. In a preferred embodiment, the dosage form is a tablet. Tablets are formed using one or more of the following: excipients which aid in the tableting process, glidants, binders, disintegrants, fillers, diluents and lubricants.

The application of coating compartments of the present invention to Valerian tablet core using a perforated coating pan is described below. Each coating layer may be applied to Valerian tablets utilizing the commonly used perforated coating pan system equipped with the spray nozzle assembly. Core (uncoated) tablets are placed inside the coating pan and the coating pan is rotated at a selected speed to provide movement of the tablets. A pump device is used to deliver coating solution or suspension at a selected rate to the spray nozzle assembly. With the presence of compressed air through the spray nozzle assembly, coating solution or suspension is atomized into small droplets or mists when coming out from the nozzle tip. Airflow pre-heated to the desired temperature and controlled at the desired flow rate is applied to the tablets throughout the coating run to assist evaporation of the coating solvent(s). The evaporation of coating solvent(s) causes solids in coating solution or suspension to deposit on the tablet surface and form the protective film or layer around the tablets. Cleaning of the product contact surface inside the coating pan within or between coating layers may be required to minimize contact of odor carrying materials from pan surface to coated tablet surface.

Odor-masking efficiency can be verified easily by comparing the smell of tablets before and after coating. The presence of a strong, unique, and unpleasant odor is a very specific characteristic of the uncoated tablets containing Valerian extracts. Tablet samples before and after odor-masking coating may also be separately packaged into high density polyethylene bottles, sealed, and stored at room temperature for a pre-determined time period. The odor between coated and uncoated tablets can be compared by smelling the samples immediately after opening the sealed bottles.

The benefits of the odor-masking system described herein include, but are not limited to:

1. The complicated multiple-stage coating process employed for traditional sugar-coating operation may be eliminated or substantially simplified. For example, this odor-masking technique of the present invention does not need to incorporate sealing coat polishing layer, and gross coat as typically required in sugar coating.
2. Each layer may be applied in various combination or sequence or even a single layer with slight modification in applied amount.
3. The coating system and operation technique are widely used in pharmaceutical industry. No special training or parts are required.
4. Proposed coating materials are commonly used in pharmaceutical industry and can be substituted with other similar compounds in the same chemical group.
5. Coating amount can be easily controlled or modified to achieve the desired odor-masking criteria.

The extract produced, and preferably the tablets produced according to the methods of the present invention advantageously may be administered to an individual in a dose containing a pharmaceutically-effective amount of Valerian, Valerian extract, or component(s) therein. This administration can be through any effective route. It is contemplated that administration may be effected, for example, preferably orally, but also may also be administered intramuscularly, subcutaneously, intraperitoneally, transdermally, transmucosally, buccally, or through inhalation or pulmonary infusion. Dosages that are contemplated for a 70 kg adult human range from a lower limit of 10, 25, 50, 100, 150, 200, or 250 mg to an upper limit of 750, 1000, 1500, 2000, 2500, 3000, 4000, 5000, or up to 10,000 mg. of the compositions described herein, or other extracts of valerian. Preferred dosages for a 70 kg human are from about 100, 200, or 250 mg to about 1000, 1500, 2000, or 2500 mg. These dosages can be administered once, twice or up to four times per day, or two or more dosages may be combined. The dose may also be tailored to achieve a desired effect, but will depend on such factors as weight, diet, concurrent medication and other factors which those skilled in the medical arts will recognize.

The present invention also encompasses pharmaceutical compositions comprising a pharmaceutically acceptable carrier prepared for storage and subsequent administration, which have a pharmaceutically effective amount of the extract disclosed above in a pharmaceutically acceptable carrier or diluent. Acceptable carriers or diluents for therapeutic use are well known in the pharmaceutical art, and are described, for example, in *Remington's Pharmaceutical Sciences* (A. R. Gennaro edit. 1985), Mack Publishing Co, Easton, Pa., or latest edition. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

These compositions may be formulated and used as, preferably, tablets, and also as capsules for oral administration. Suitable additional excipients are, for example, water, saline, dextrose, mannitol, lactose, lecithin, albumin, sodium glutamate, cysteine hydrochloride, and the like. In addition, if desired, the pharmaceutical compositions may contain relatively small amounts of nontoxic auxiliary substances, such as wetting agents, pH buffering agents, and the like.

In practicing the compositions of the invention, the formulated dosage may be used alone or in combination with other therapeutic or diagnostic agents. These products can be utilized in vivo, ordinarily in a mammal, preferably in a human, or in vitro. In employing them in vivo, the products or compositions can be administered to the mammal in any of a variety of manners known to persons skilled in the art, and may employ any of a variety of dosage forms.

As will be appreciated by those of skill in the art, the methods described herein may be combined or complimented by other odor-reducing techniques, such as those described in U.S. patent application Ser. No. 60/173,983, Entitled "Process For Reducing The Odor Of Valeriana" filed on this date and herewith, the disclosure of which is hereby incorporated by reference herein.

EXAMPLE 1

An example of a Valerian tableting formulation for a tablet core is described below and in Table 1.

TABLE 1

| Ingredient | Concentration (mg/tablet) | Percent | Commercial Source |
|---|---|---|---|
| Valerian Extract | 250.00 | 50.00 | Described Herein |
| Colloidal Silicon Dioxide (Cab-O-Sil), M5P | 1.50 | 0.30 | Cabot Corp. |
| Povidone K-30 | 30.00 | 6.00 | ISP |
| Croscarmellose Sodium, Type A | 10.00 | 2.00 | FMC Corp. |
| Lactose Monohydrate Spraydried (Fast-flo 316) | 204.50 | 40.90 | Foremost |
| Magnesium Stearate | 4.00 | 0.80 | Mallinckrodt |

The additional tablet components listed in Table 1 were weighed out and, if deemed necessary due to non-uniform consistency, as would be appreciated by those of skill in the art, milled individually to a uniform consistency. First, dried valerian extract, prepared as described herein, was milled through a 0.045" round hole screen and put into a blender. The colloidal silicon dioxide and a portion of the lactose monohydrate were hand-sieved through a #20 mesh screen. These were combined with the dried Valerian extract in the blender and blended for approximately 10±2 minutes. Next, the croscarmellose sodium, Povidone K-30, and a second portion of lactose monohydrate were milled through a 0.045" round-hole screen using a smooth impeller. The aforementioned components were all combined and blended for approximately 15±2 minutes. The magnesium stearate and the last portion of the lactose monohydrate were then hand-sieved through a #20 mesh screen and added to the powder blend. The components were then blended for an additional 3±1 minutes to achieve a mixture and sampled for testing. The mixture was compressed into core tablets using a multiple-station tablet press and 0.4375" round, plain, standard concave tooling and under the following conditions: tablet press speed, 60±5 rpm (mean table weight, 500±15 mg); mean tablet hardness, 8±2 Kp; mean tablet thickness, 0.192±0.005"; tablet friability, <0.8%.

Once the core tablets were prepared, and not more than 24 hours before application, suspensions of the three coatings described in Tables 2–4, and the optional Opadry II coating (coatings 4, 6, 8 and 10 in FIG. 1), were individually and separately prepared.

EXAMPLE 2

An example of a composition of the first coating compartment (coating #1), as shown schematically as 4 in FIG. 1, is described below and in Table 2.

TABLE 2

| Preferred Composition | | Example | |
|---|---|---|---|
| Ingredient | % w/w | Ingredient | % w/w |
| Hydroxypropyl cellulose or Hydroxyethyl cellulose | 10–70 | Klucel EXF (Hercules, Aqualon Division) | 50 |
| Hydroxypropyl methylcellulose | 0–20 | Methocel E4M Prem. (Dow Chemical) | 1 |
| Plasticizer | 0–20 | Polyethylene Glycol 8000 (Union Carbide) | 1 |
| Anti-tackiness agent | 20–60 | Talc (Alphafil 500) (Luzanac America) | 48 |

Water is the preferred solvent for the above example. Coating #1 was prepared by adding hydroxypropyl methylcellulose to the initial portion of purified water and mixing for at least 20 minutes. Hydroxypropyl cellulose was then dispersed into the solution and mixed for 5±1 minutes. The mixing speed was then reduced and continued for at least 30 minutes, then stopped for at least 60 minutes, a time sufficient to defoam. Mixing was then resumed and polyethylene glycol 8000 was added and agitated for at least 15 minutes. Talc was then added and mixed for at least 15 minutes before coating application, and mixing continued until end of coating application.

EXAMPLE 3

An example of the composition of the second coating compartment (Coating #2), as shown schematically as 6 in FIG. 1, is described below and in Table 3.

TABLE 3

| Preferred Composition | | Example | |
|---|---|---|---|
| Ingredient | % w/w | Ingredient | % w/w |
| Sucrose | 20–80 | Sucrose (Domino Sugar Corporation) | 40 |
| Polyvinyl pyrrolidone | 0–30 | Povidone K-30 (ISP) | 10 |
| Plasticizer | 0–20 | Polyethylene Glycol 8000 | 8 |
| Anti-tackiness agent | 5–30 | Colloidal Silicon dioxide (Cab-O-Sil), M5P (Cabot Corporation) | 10 |
| Anti-tackiness agent | 5–50 | Talc (Alphafil 500) | 32 |

The preferred solvent for the above example is water. Coating #2 was prepared by adding polyethylene glycol 8000 to a second portion of purified water and mixing for at least 15 minutes. This was followed by the addition of povidone K-30 and a mixing time of at least 15 minutes, sucrose and a mixing time of at least 10 minutes, colloidal silicone dioxide and a mixing time of at least 15 minutes before coating application. As in Example 2, mixing continued until end of coating application.

EXAMPLE 4

An example of the composition of the third coating compartment (Coating #3), as shown schematically as 8 in FIG. 1, is described below and in Table 4.

TABLE 4

| Preferred Composition | | Example | |
|---|---|---|---|
| Ingredient | % w/w | Ingredient | % w/w |
| Polymethacrylate | 1–30 | Eudragit NE30D (Rohm) | 9* |
| Hydroxypropyl cellulose | 5–70 | Klucel EXF | 40 |
| Hydroxypropyl methylcellulose | 0–20 | Methocel E4M, Prem. | 1 |
| Plasticizer | 0–20 | — | — |
| Anti-tackiness agent | 10–70 | Talc (Alphafil 500) | 50 |

*Percent w/w of Eudragit NE30D refers to solid weight excluding solvent

Water is the preferred solvent for the above example. Coating #3 was prepared by first adding hydroxypropyl methylcellulose to the third portion of purified water and mixing for at least 20 minutes. Hydroxypropyl cellulose was then added and mixed for 5±1 minutes. The mixing speed was reduced and mixing was continued for at least 30 minutes, then stopped for at least 60 minutes, a time sufficient to defoam. Mixing was then resumed and polyacrylate dispersion, 30%, and talc were added and agitated for at least 15 minutes before coating application. As in Examples 2 and 3, mixing continued until end of coating application.

The last solution, coating #4, was prepared by adding Opadry II to the final aliquot of purified water and mixing for at least 15 minutes at high speed, then 15 minutes at a lower speed. Mixing was then terminated.

15 kg of coating #1 was applied in 2 applications to a final target weight gain of about 10% w/w of core tablet using parameters shown in Table 5:

TABLE 5

| Conditions | Target |
|---|---|
| Coater (CompuLab-brand, Thomas Engineering) | 24 inch coating pan |
| Pan load | 12.0 kg |
| Gun to Bed Distance | 5–11" |
| Inlet air flow | 475 cfm |
| Pan Speed | 7 rpm |
| Inlet air temperature | 65° C. |
| Outlet air temperature | 43° C. |
| # of spray guns | 2 |
| spray rate/gun | 20 g/min/gun |
| Atomizing air pressure | 40 psi |
| pattern air | 50 psi |

The two-stage application allowed for a cleaning step of the coating pan in the middle of the coating application which removed the characteristic odor from the pan and facilitated the odor-masking function of the coating process.

10 kg of Coating #2 was applied to a target weight gain of about 10% w/w of core tablet using the same parameters as Coating #1, with the exception that the target pan load was 13.2 kg.

4.5 kg of Coating #3 was applied to a target weight gain of about 3% w/w of core tablet using the same parameters as Coating #2, with the exception that the target pan load was 14.4 kg and the pan speed was 8 rpm.

Finally, 1.8 kg of Coating #4 (Opadry II) was applied to a target weight gain of about 3% w/w of core tablet using the same parameters as Coating #3, with the exception that the target pan load was 14.8 kg.

The tablets were dried between coating applications and sampled to ensure a target mean weight. The mean tablet weights after completion of coatings #1–4 were 538–560 mg, 583–615 mg, 596–632 mg and 609–649 mg, respectively.

EXAMPLE 5

TABLET STABILITY

Valerian extract tablets having the composition described in Table 1 and coated with the coating compartments described in Tables 2, 3, 4 and an outer, optional OpadryII (32K 11498) coating compartment were tested for long-term stability under different storage conditions to monitor physical integrity, seepage of the characteristic Valeriana odor and chemical integrity. The tablets were packaged as bulk (in polyethylene bags contained in fiber drums) and in blister cards with one tablet per blister. Samples of both were stored at 25° C./60% relative humidity and at 40° C./75% relative humidity.

The results of the stability testing for a period of six months are summarized below in Tables 6 and 7, for tablets stored in standard blister cards and tablets stored in bulk, respectively. The results clearly indicate that the coating process, optimized to block the characteristic odor of valerian root extract, is stable both physically and chemically for a period of at least 6 months when stored either at normal room conditions or at the condition of 40° C. and 75% relative humidity, which one of skill in the art would expect to accelerate degradation. Most importantly, the characteristic odor of valerian root does not "seep out" of the composite coating, as it was not detected. Higher moisture content increases the hardness of the coating as evidenced by higher disintegration times ($\leq 60$ min at 6 months as compared to $\leq 45$ min initially) of the tablets stored in bulk (See especially Table 7.).

TABLE 6

Stability of Tablets Stored in Blister Cards

| | | | 1 month | | | | 3 month | | | | 6 month | | | |
|---|---|---|---|---|---|---|---|---|---|---|---|---|---|---|
| | | | 25°/60% RH replicate | | 40°/75% RH replicate | | 25°/60% RH replicate | | 40°/75% RH replicate | | 25°/60% RH replicate | | 40°/75% RH replicate | |
| TEST | SPECIFI-CATION | Initial | 1 | 2 | 1 | 2 | 1 | 2 | 1 | 2 | 1 | 2 | 1 | 2 |
| Total Valerenic Acids (mg/tablet) | 0.75–2.00 | 1.72 ± 0.05 | 1.7 | 1.7 | 1.7 | 1.7 | 1.7 | 1.7 | 1.6 | 1.7 | 1.7 | 1.7 | 1.7 | 1.7 |
| Moisture Content (%) | $\leq 5\%$ | 3.88% | 3.52 | 3.80 | 3.95 | 3.84 | 4.20 | 4.32 | 4.91 | 4.82 | 4.33 | 4.29 | 4.82 | 4.89 |
| Appearance, Color, Odor | round, bi-convex, plain, green color, coated tablets, odorless | round, bi-convex, plain, green color, coated tablets, odorless | no change | no change | no change | no change | no change | no change | no change | no change | no change | no change | no change | no change |
| Disintegration | $\leq 45$ min | $\leq 45$ min | $\leq 45$ min | | $\leq 45$ min | | $\leq 45$ min | | $\leq 45$ min | | $\leq 45$ min | | $\leq 45$ min | |

TABLE 7

Stability of Tablets Stored in Bulk

| | | | \multicolumn{4}{c|}{1 month} | \multicolumn{4}{c|}{3 month} | \multicolumn{4}{c|}{6 month} |
|---|---|---|---|---|---|---|---|---|---|---|---|---|---|---|
| | | | 25°/60% RH replicate | | 40°/75% RH replicate | | 25°/60% RH replicate | | 40°/75% RH replicate | | 25°/60% RH replicate | | 40°/75% RH replicate | |
| TEST | SPECIFI-CATION | Initial | 1 | 2 | 1 | 2 | 1 | 2 | 1 | 2 | 1 | 2 | 1 | 2 |
| Total Valerenic Acids (mg/tablet) | 0.75–2.00 | 1.72 ± 0.05 | 1.7 | 1.7 | 1.7 | 1.7 | 1.7 | 1.7 | 1.8 | 1.7 | 1.7 | 1.7 | 1.7 | 1.7 |
| Moisture Content (%) | ≦5% | 3.88% | 4.16 | 4.34 | 4.42 | 4.28 | 5.79 | 6.19 | 6.17 | 6.01 | 5.31 | 5.57 | 6.9 | 7.03 |
| Appearance, Color, Odor | round, bi-convex, plain, green color, coated tablets, odorless | round, bi-convex, plain, green color, coated tablets, odorless | no change | no change | no change | no change | no change | no change | no change | no change | no change | no change | no change | no change |
| Disintegration | ≦45 min | ≦45 min | ≦45 min | | ≦45 min | | ≦45 min | | ≦45 min | | ≦45 min | | ≦45 min | |

Although the present invention has been described in terms of certain preferred embodiments, other embodiments which will be apparent to those of ordinary skill in the art in view of the disclosure herein are also within the scope of the present invention. Accordingly, the scope of the invention is intended to be defined only by reference to the appended claims.

The various articles of the scientific and/or medical literature, texts, and the U.S. and foreign patents and patent applications cited herein are hereby incorporated by reference; each constitutes a part of the disclosure of this specification. Furthermore, while specific embodiments, and working and prophetic examples of the invention have been described in detail to illustrate the broad applicability and principles underlying the invention, it will be understood by those of skill in the art that the invention may be embodied otherwise without departing from such broad applicability and principles.

What is claimed is:

1. A tablet comprising
a pharmaceutically effective amount of an extract of the root of Valerian; and
a pharmaceutically-inert coating comprising one or more of the following coating compartments: a first coating compartment comprising a hydroxyalkyl cellulose wherein the alkyl group has between 1 and 10 carbon atoms, and an anti-tackiness agent; a second coating compartment comprising a sugar and at least one anti-tackiness agent; and a third coating compartment comprising a methacrylate copolymer, a hydroxyalkyl cellulose and an anti-tackiness agent.

2. The tablet of claim 1, wherein the coating further comprising a coating compartment that is colored, flavored, or scented.

3. The tablet of claim 1, wherein said hydroxyalkyl cellulose is selected from the group consisting of hydroxyethyl cellulose and hydroxypropyl cellulose.

4. The tablet of claim 1, wherein said anti-tackiness agent is selected from the group consisting of talc, silicon dioxide, silica hydrogel, microcrystalline cellulose, alkali stearates, and starch.

5. The tablet of claim 1, wherein said sugar is selected from the group consisting of sucrose, dextrose, dextrin, maltose, glucose, fructose, mannose, sorbitol, lactose, mannitol, and xylose.

6. The tablet of claim 1, wherein said methacrylate copolymer is selected from the group consisting of the methacrylic acid copolymers, the aminoalkylmethacrylate copolymers, and the ammoniomethacrylate copolymers.

7. The tablet of claim 1, wherein said first coating compartment further comprises a compound which facilitates the coating process.

8. The tablet of claim 1, wherein said first coating compartment further comprises hydroxypropyl methylcellulose.

9. The tablet of claim 1, wherein first coating compartment further comprises a plasticizer.

10. The tablet of claim 9, wherein said plasticizer is selected from the group consisting of propylene glycol, glycerin, trimethylolpropane, polyethylene glycols, dibutyl sebacate, acetylated monoglycerides, diethylphthalate, triacetin, glyceryl triacetate, acetyltriethyl citrate and triethyl citrate.

11. The tablet of claim 1, wherein said second coating compartment further comprises an agent which facilitates the coating process.

12. The tablet of claim 11, wherein said agent is selected from the group consisting of polyvinyl pyrrolidone, vinylpyrrolidone acetate copolymer, vinyl acetate-crotonic acid copolymer, ethyl acrylate-methacrylic acid copolymer, hydroxypropyl cellulose, gelatin, acacia, an ethylcellulose, and a methylcellulose.

13. The tablet of claim 1, wherein said second coating compartment comprises a plasticizer.

14. The tablet of claim 13, wherein said plasticizer is selected from the group consisting of propylene glycol, glycerin, trimethylolpropane, polyethylene glycols, dibutyl sebacate, acetylated monoglycerides, diethylphthalate, triacetin, glyceryl triacetate, acetyltriethyl citrate and triethyl citrate.

15. The tablet of claim 1, wherein said second coating compartment comprises talc and a second anti-tackiness agent.

16. The tablet of claim 1, wherein said second coating compartment comprises silicon dioxide and a second anti-tackiness agent.

17. The tablet of claim 1, wherein said third coating compartment further comprises hydroxypropylmethyl cellulose.

18. The tablet of claim 1, wherein said third coating compartment further comprises a plasticizer.

19. The tablet of claim 18, wherein said plasticizer is selected from the group consisting of propylene glycol, glycerin, trimethylolpropane, polyethylene glycols, dibutyl sebacate, acetylated monoglycerides, diethylphthalate, triacetin, glyceryl triacetate, acetyltriethyl citrate and triethyl citrate.

20. The tablet of claim 1, wherein said third coating compartment comprises a water soluble polymer or compound.

21. The tablet of claim 20, wherein said water soluble polymer is selected from the group consisting of hydroxypropyl cellulose, hydroxypropyl methylcellulose, acacia, sodium carboxymethylcellulose, dextrin, alginic acid, ethylcellulose resin, gelatin, guar gum, liquid glucose, methylcellulose, pregelatinized starch, sodium alginate, starch, zein, polyvinylpyrrolindone, vinylpyrrolidone-vinyl acetate copolymer, vinyl acetate-crotonic acid copolymer and ethyl acrylate-methacrylic acid copolymer.

22. A tablet comprising a pharmaceutically effective amount of an extract of the root of Valerian; and a pharmaceutically-inert coating comprising a hydroxyalkyl cellulose wherein the alkyl group is selected from the group consisting of methyl, ethyl and propyl groups.

23. The tablet of claim 22, wherein the hydroxyalkyl cellulose serves to control the release of the pharmaceutically effective amount of an extract of the root of Valerian.

24. A tablet comprising a pharmaceutically effective amount of an extract of the root of Valerian; and a pharmaceutically-inert coating comprising at least one of the following coating compartments: a first coating compartment means for enhancing the viscosity of the extract; a second coating compartment means for enhancing the palatability of the tablet; and a third coating compartment means for effecting controlled release of the extract.

25. The tablet of claim 22, wherein the hydroxyalkyl cellulose is hydroxypropyl methylcellulose.

26. The tablet of claim 22, wherein the coating further comprises a colorant.

27. The tablet of claim 22, wherein the coating further comprises a scent.

28. The tablet of claim 22, wherein the coating further comprises a flavoring agent.

* * * * *